US005478925A

United States Patent [19]
Wallach et al.

[11] Patent Number: 5,478,925
[45] Date of Patent: Dec. 26, 1995

[54] MULTIMERS OF THE SOLUBLE FORMS OF TNF RECEPTORS, THEIR PREPARATION AND PHARMACEUTICAL COMPOSITIONS CONTAINING THEM

[75] Inventors: David Wallach, Rehovot, Israel; Cord Brakebusch, Braunschweig, Germany

[73] Assignee: Yeda Research and Development Co. Ltd., Rehovot, Israel

[21] Appl. No.: 925,687

[22] Filed: Aug. 7, 1992

[30] Foreign Application Priority Data

Aug. 7, 1991 [IL] Israel .......................................... 99120

[51] Int. Cl.$^6$ ........................... C07K 14/525; A61K 45/00
[52] U.S. Cl. ........................ 530/351; 424/85.1; 424/450; 424/158.1
[58] Field of Search .................................... 530/351, 817; 424/85.1, 450, 158.1

[56] References Cited

U.S. PATENT DOCUMENTS 4,837,028  6/1989  Allen ........................................ 424/450

FOREIGN PATENT DOCUMENTS

| 186833 | 12/1985 | European Pat. Off. . |
| 308378 | 9/1988 | European Pat. Off. . |
| 398327 | 5/1990 | European Pat. Off. . |
| 418014 | 9/1990 | European Pat. Off. . |
| 433900 | 12/1990 | European Pat. Off. . |
| 73833 | 12/1984 | Israel . |

OTHER PUBLICATIONS

Loetscher et al. 1991 J. Biol Chem. 266:18324–18329.
Peppel et al. 1991 J. Exp. Med. 174:1483–1489.
Peppel et al. 1993 J. Immunology 151:5699–5703.
Lesslauer et al. 1991 Eur. J. Immunol 21:2883–2886.
Mohler et al 1993 J. Immunol 151:1548–1561.
Seckinger et al. 1989 J. Biol. Chem. 264:11966–11973.
Engelmann et al 1990 J. Biol. Chem. 265:1531–1536.
Himmler et al. 1990 DMNA Cell Biol. 9: 705–715.
Utsumi et al 1991 Cancer Res 51:3362–3366.
Debs et al 1989 J. Immunol. 143:1192–1197.
Smith et al. 1989 J. Biol. Chem. 264:14646–14652.
B. Beutler, A. Cerami, "Tumor, Necrosis, Cachexia, Shock, and Inflammation: A Common Mediator," Annual Review Biochemistry, 1988, 57:505–518.
L. J. Old, "Tumor Necrosis Factor", Scientific American, 1988, 258:41–49.
J. Frere, C. Gerday, "Les Methodes de Purification et d'Analyse des Proteines", Masson, Paris, France 1981, pp. 48–49.

Primary Examiner—Stephen G. Walsh
Assistant Examiner—K. Cochrane Carlson
Attorney, Agent, or Firm—Browdy and Neimark

[57] ABSTRACT

Multimers of the soluble forms of the tumor necrosis factor receptors (TNF-Rs) are provided. These multimers are produced either by chemical or by recombinant methods. The multimers of the soluble forms of TNF-Rs are useful for protecting mammals (including humans) from the deleterious effects of TNF.

7 Claims, 5 Drawing Sheets

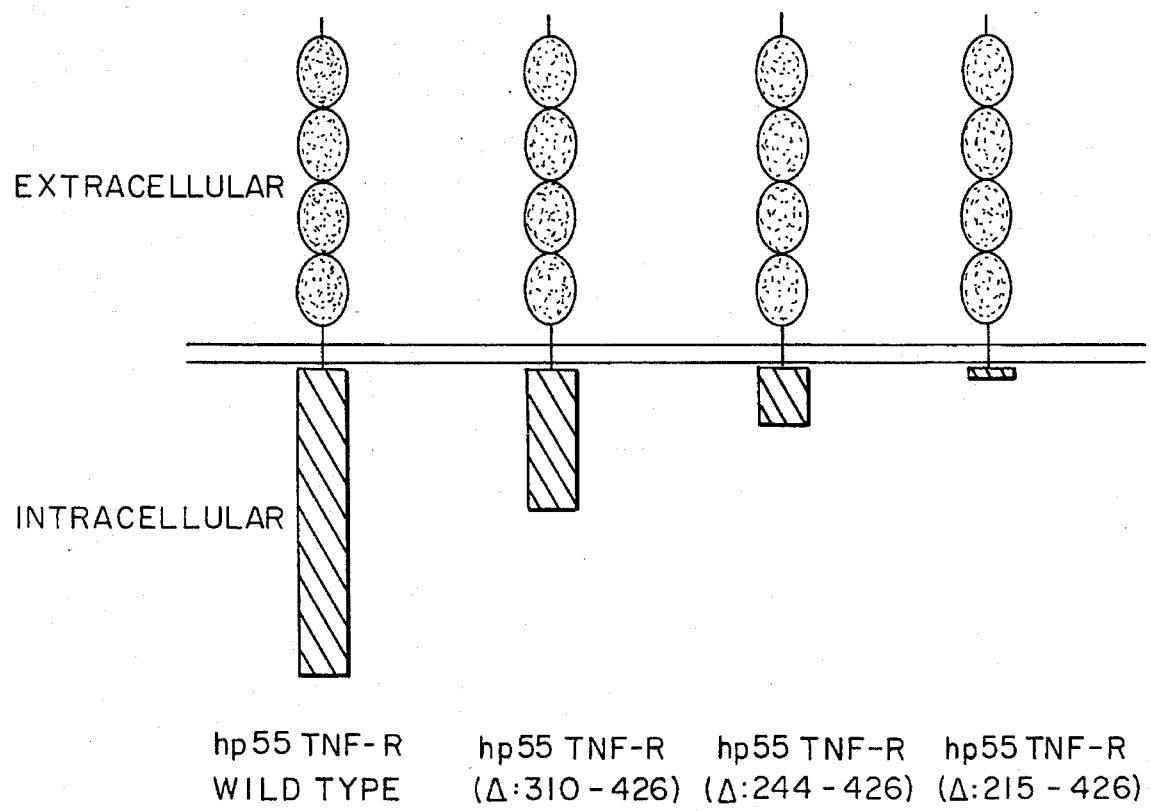

Effect of TNF

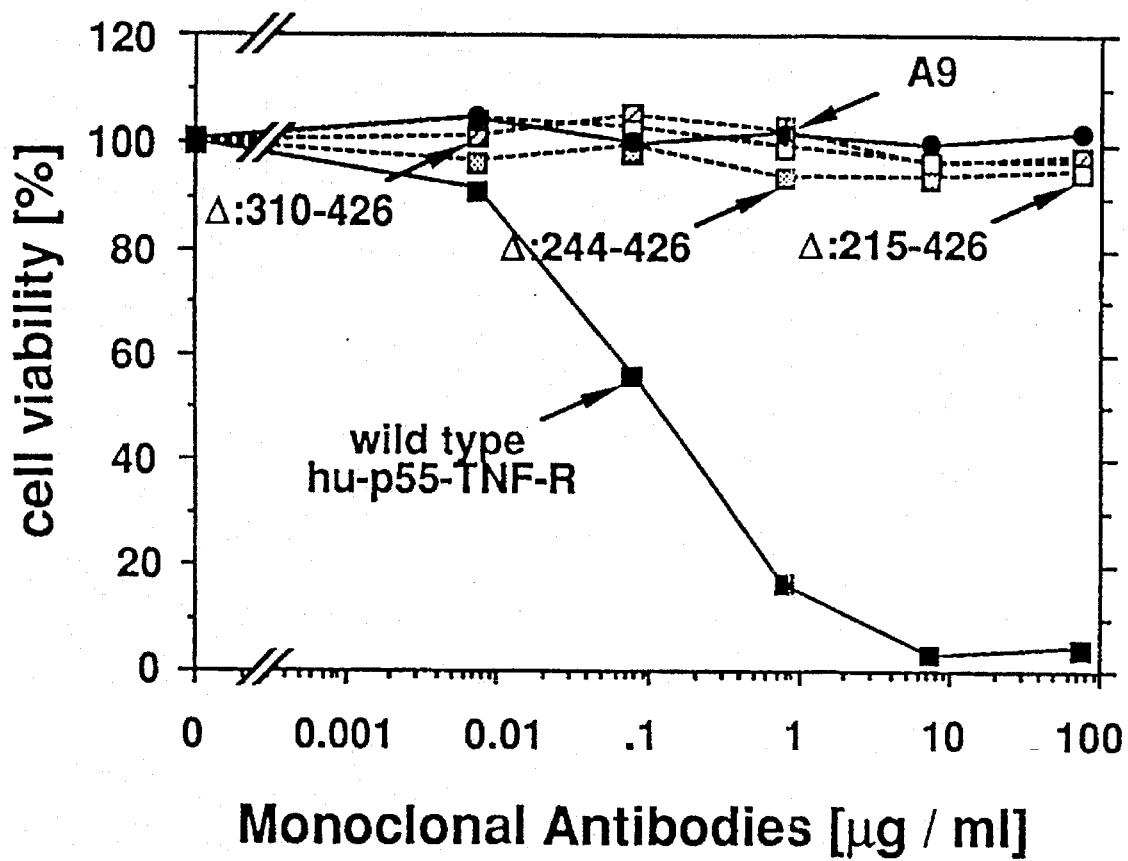

MULTIMERS OF THE SOLUBLE FORMS OF TNF RECEPTORS, THEIR PREPARATION AND PHARMACEUTICAL COMPOSITIONS CONTAINING THEM

FIELD OF THE INVENTION

The present invention relates to multimers of the soluble forms of the tumor necrosis factor receptors, their preparation and pharmaceutical compositions containing them.

BACKGROUND OF THE INVENTION

Tumor necrosis factor (TNF) is a cytokine produced by a number of cell types, primarily by mononuclear phagocytes. At present, two different TNFs have been identified: TNF-α and TNF-β (lymphotoxin). Both TNF-α and TNF-β initiate their effects by binding to specific cell receptors.

TNF-α and TNF-β (hereinafter called "TNF") are known to exert both beneficial as well as deleterious effects on a number of different target cells involved in the inflammatory response. Among its many effects, TNF, for example, stimulates the growth of fibroblasts and induces in these cells the synthesis of collagenase, prostaglandin E2 and IL-6. TNF also decreases in adipocytes the activity of lipoprotein lipase, activates osteoclasts and increases in endothelial cells adhesivity for blood leukocytes.

However, TNF has also extremely deleterious effects: over-production of TNF can play a major pathogenic role in several diseases, for example, TNF-α is known to be a major cause for the symptoms of septic shock. In some diseases, TNF may cause excessive loss of weight (cachexia) by suppressing activities of adipocytes and by causing anorexia (TNF-α was therefore called cachectin). See, e.g. Beutler et al., Annu. Rev. Biochem., 57, pp. 507–518 (1988) and Old, Sci. Am. 258, pp. 41–49 (1988). Excessive TNF production has also been demonstrated in patients with AIDS.

In order to counteract the cytotoxic effects of TNF, ways were sought to antagonize or eliminate endogenously formed or exogenously administered TNF. Furthermore, ways are being sought to induce specifically only some of the many effects of TNF or restrict its action to a specific kind of target cells. The first attempt in this direction was the development of monoclonal antibodies which neutralize the TNF-α cytotoxic activity. Such monoclonal antibodies are described in EP 186 833 and in Israel Patent No. 73883.

As stated above, TNF initiates its function by binding to specific cell surface receptors. Two such TNF receptors (hereinafter "TNF-R") which are expressed differentially in cells of different kinds are known, the p55-TNF receptor and the p75-TNF receptor (p55-TNF-R and p75-TNF-R). Two proteins called TBP-I and TBP-II which bind specifically to TNF have been shown to cross-react immunologically with the two receptors. Both proteins provide protection against the in vitro cytocidal effect of TNF and both bind TNF-β less effectively than TNF-α. It was found that the formation of the TBPs occurs by proteolytic cleavage of the cell surface TNF-Rs, resulting in release of a major part of their extra-cellular domain (see EP 308 378, 398 327 and 444,900). Indeed, the sequences of the amino acids in TBP-I and TBP-II were found to be fully identical to sequences found in the extra-cellular domains of the cell-surface receptors, but do not contain any part of the intracellular domain of the receptors.

These findings imply that the inhibition of TNF function by TBP-I and TBP-II reflects the conservation, in TBP-I and TBP-II, of part of the structural features of the cell surface TNF-Rs, which are important for binding of TNF by the receptors and the initiation of cell response to TNF thereby. Due to this conservation of structure, TBP-I and TBP-II have the ability to compete with the cell surface TNF-Rs for TNF and thus block its function.

It is known that TNF, in its natural state, exists as a multimer (trimer) consisting of three identical polypeptide chains, each with a molecular size of about 17,000 D.

To elicit its effects, TNF must bind to the TNF Receptors in its trimeric form. Although the TNF monomer also binds to cells (but at a lower affinity when compared with the TNF trimer), it has no effect.

SUMMARY OF THE INVENTION

The present invention now provides multimers of the soluble forms of the TNF-Rs, and salts for functional derivatives thereof. These multimers, effectively interfere with the binding of TNF to the cell-surface receptors and thus do not allow TNF to exert its deleterious effect.

The term "multimers" as used herein refers to any combination of monomers held together, for example, by covalent bonding, liposome formation, the incorporation of monomers of the soluble form of TNF-R into a single recombinant soluble, or any other combination of monomers.

The multimers may either be in dimeric, trimeric or other multimeric form and may comprise, for example, TBP-I, TBP-II, or mixtures thereof.

The invention also provides methods of producing these multimers by covalent cross-linking of the soluble forms of the TNF-Rs.

In another aspect, the present invention relates to DNA molecules comprising the nucleotide sequences encodin the multimers of the soluble forms of the TNF-Rs, to expression vehicles comprising them, to host cells transformed therewith, and to processes for producing the multimers by culturing the transformed cells in a suitable culture medium.

The invention further relates to nucleic acid, such as DNA or RNA, which hybridizes to DNA or RNA which encodes a multimer in accordance with the present invention, under stringent conditions. Such nucleic acid is useful as a probe in identification and purification of the desired nucleic acid. Furthermore, such nucleic acid would be a prime candidate to determine whether it encodes a polypeptide which retains the functional activity of the multimers of the present invention. The term "stringent conditions" refers to hybridization and subsequent washing conditions which those of ordinary skill in the art conventionally refer to as "stringent". See Ausubel et al., Current Protocols in Molecular Biology, Greene Publishing Associates and Wiley Interscience, N.Y., §§6.3 and 6.4 (1987, 1992), and Sambrook et al., supra. Without limitation, examples of stringent conditions include washing conditions 12°–20° C. below the calculated Tm of the hybrid under study in, e.g., 2×SSC and 0.5% SDS for 5 minutes, 2×SSC and 0.1% SDS for 15 minutes; 0.1×SSC and 0.5% SDS at 37° C. for 30–60 minutes and then a 0.1×SSC and 0.5% SDS at 68° C. for 30–60 minutes. Those of ordinary skill in this art understand that stringency conditions also depend on the length of the DNA sequences, oligonucleotide probes (such as 10–40 bases) or mixed oligonucleotide probes. If mixed probes are used, it is preferable to use tetramethyl ammonium chloride (TMAC) instead of SSC. See Ausubel, supra.

The multimers according to the invention, and the salts and functional derivatives thereof, may comprise the active ingredient of pharmaceutical compositions for protecting mammals from the deleterious effects of TNF. These compositions are yet another aspect of the present invention.

DETAILED DESCRIPTION OF THE INVENTION

As stated hereinbefore, TNF exists and exerts its biological action as a trimer. However, nothing has been known so far as to the form of the TNF-Rs to which TNF binds, i.e. whether the TNF trimer binds to individual molecules of the TNF-Rs, or the receptors themselves also exist as multimers or become multimers following TNF binding which better accommodates the TNF trimers.

We have now found that the TNF-Rs exist in aggregated forms in cells exposed to TNF.

This was shown by analysis of full-length and C-terminal truncated forms of the human p55-TNF-Rs tagged by cross-linking to labelled TNF. For this purpose we produced truncated forms of the human p55-TNF-R by site-directed mutagenesis of the cDNA and expressed them in murine A9 cells. Radiolabelled TNF was applied on these cells and cross-linked chemically to the TNF-Rs. The TNF-Rs were solubilized with a detergent, and antibodies specific to the human receptors were applied to immunoprecipitate the human receptors, examining thereby whether murine receptors associate noncovalently with the human receptor as a consequence of aggregation of the receptors.

TBP-I and TBP-II monomers must be administered in very high doses in order to result in effective inhibition of TNF-binding to cells in the human body. The multimers of the soluble forms of TNF-Rs according to the invention, are believed to be more effective in inhibiting TNF activity at lower doses, since they can effectively compete with the TNF trimers for the binding sites on the aggregates of the cell surface TNF-Rs.

The multimers of the soluble forms of the TNF-Rs may be produced chemically by using known methods which will result in the formation of either dimers or higher multimers of the soluble forms of the TNF-Rs.

Another way of producing the multimers of the soluble forms of the TNF-Rs is by recombinant techniques. In this way, massive production of multimers with optimal TNF binding activity will be made possible.

The multimers of the present invention have the ability to interfere with the binding of TNF to its receptors and/or to block the effects of TNF. Each multimer comprises two or more monomers, each comprising the soluble form of a TNF-R or a salt or functional derivative thereof. The upper limit for the number of monomers in a multimer is not important and liposomes having many such monomers thereon may be used. Such multimers preferably have 2–5 monomers and more preferably 2 or 3.

Each monomer of the multimer is a soluble form of a TNF-R or a salt or functional derivative thereof. Preferably, the monomers are TBP-I and/or TBP-II or their salts or functional derivatives. More preferably, each monomer is a protein having an amino acid sequence essentially corresponding to that of TBP-I or TBP-II and, most preferably, exactly corresponding to TBP-I and TBP-II. The term "essentially corresponding to" is intended to comprehend proteins with minor changes to the sequence of the natural protein which do not affect the basic characteristics of the natural protein insofar as its ability to bind to TNF is concerned and to thereby inhibit the binding of TNF to a natural TNF receptor in situ. The type of changes which are generally considered to fall within the "essentially corresponding to" language are those which would result from conventional mutagenesis techniques of the DNA encoding these proteins, resulting in a few minor modifications, and screening for the desired activity.

All of the monomers in the multimer may be TBP-I or a polypeptide essentially corresponding to TBP-I or they may all be TBP-II or a polypeptide essentially corresponding to TPB-II. Alternatively, the monomers of a given multimer may comprise a mixture of TBP-I and TBP-II monomers.

As indicated above, the term "multimer" is intended to include molecules including at least two of the defined monomers, which monomers may be linked by any of various methods. For example, the monomers may be chemically cross-linked by means of known linker molecules. Those of ordinary skill in the art will be able to determine the optimum length of any such linker molecules to produce multimers which best bind to the TNF trimer. Similarly, if the multimer is produced by recombinant techniques, the DNA which encodes each monomer may be linked in the manner well known for the production of fusion proteins so that the entire multimer will be encoded by a single DNA molecule which is present in a replicable expression vehicle in a manner to permit expression of the multimer in a transformant host cell, which host cell may be either prokaryotic or eukaryotic. Again, the nature of the amino acids which link the monomers in the recombinantly produced multimer is not critical and the optimum length of such linkers in such recombinantly produced proteins can also be determined by routine experimentation.

The term "multimer" is also intended to include pharmaceutically administrable aggregates of monomers having the ability to interfere with the binding of TNF to its receptors and to block the effects of TNF such as on the surface of liposomes. Thus, while it is preferable that the monomers be directly linked, they may be indirectly linked such as by being expressed on the surface of liposomes.

Pharmaceutical compositions containing the multimers of the soluble forms of the TNF-Rs may be employed for antagonizing the deleterious effects of TNF in mammals, i.e. they serve for treating conditions where excess of TNF is either endogenously formed or exogenously administered.

Such compositions comprise the multimers of the soluble forms of the TNF-Rs according to the invention, or their salts or functional derivatives as their active ingredient. The pharmaceutical compositions are indicated for any condition of excess TNF, either endogenously produced, such as in septic shock, cachexia, graft-versus-host reactions, autoimmune diseases such as rheumatoid arthritis, and the like, or exogenously administered, i.e. administration of overdoses of TNF.

As used herein the term "salts" refers to both salts of carboxyl groups and to acid addition salts of amino groups of the protein molecule. Salts of a carboxyl group may be formed by means known in the art and include inorganic salts, for example, sodium, calcium, ammonium, ferric or zinc salts and the like, and salts with organic bases as those formed, for example, with amines, such as triethanolamine, arginine or lysine, piperidine, procaine and the like. Acid addition salts include, for example, salts with mineral acids such as for example, hydrochloric acid or sulfuric acid, and salts with organic acids such as, for example, acetic acid or oxalic acid.

"Functional derivatives" as used herein covers derivatives which may be prepared from the functional groups which occur as side chains on the residues or the N- or C-terminal groups, by means known in the art, and are included in the invention as long as they remain pharmaceutically acceptable, i.e. they do not destroy the activity of the protein and do not confer toxic properties on compositions containing it.

These derivatives may, for example, include aliphatic esters of the carboxyl groups, amides of the carboxyl groups by reaction with ammonia or with primary or secondary amines, N-acyl derivatives of free amino acid groups of the amino acid residues formed with acyl moieties (e.g. alkanoyl or carboxylic aroyl groups) or O-acyl derivatives of free hydroxyl group (for example that of seryl or threonyl residues) formed with acyl moieties.

"Functional derivatives" also comprise multimers made up of soluble forms of TNF-Rs in which changes have been introduced in the sequence of the amino acids making up the soluble TNF-Rs by any conventional method. The sequence of any such changed soluble form of TNF-R must essentially correspond to the sequence of the soluble form of TNF-R. It is understood that none of the above changes may affect the biological properties of the TNF-Rs.

The pharmaceutical compositions according to the invention are administered depending on the condition to be treated, via the accepted ways of administration. For example, in the case of septic shock, intravenous administration will be preferred, while in the case of arthritis, local injection may be indicated. The pharmaceutical compositions may also be administered continuously, i.e. by way of infusion, or orally. The formulation and dose will depend on the condition to be treated, the route of administration and the condition and the body weight of the patient to be treated. The exact dose will be determined by the attending physician.

The pharmaceutical compositions according to the invention are prepared in the usual manner, for example by mixing the active ingredient with pharmaceutically and physiologically acceptable carriers and/or stabilizers and/or excipients, as the case may be, and are prepared in dosage form, e.g. by lyophilization in dosage vials.

When the pharmaceutical composition comprises a liposome composition, the latter is adjusted so as to assure optimal interaction of the liposome with phagocytic cells, optimal accessibility of the liposomes to the circulation and/or other compartments in the body, and optimal rates of clearance of the liposomes from those compartments.

BRIEF DESCRIPTION OF THE FIGURES

FIG. 1A: precipitation with prior acidification so as to disrupt non-covalent association between receptors. Precipitation of receptors from HeLa cells (lane 1), precipitation from extracts of non-transfected A9 cells (lane 2), from extracts of A9 cells expressing the wild type human p55-TNF-R (lane 3), and from extracts of A9 cells expressing mutants of the human p55-TNF-R: the $\Delta$:310–426 human p55-TNF-R (lane 4), the $\Delta$:244–426 human p55-TNF-R (lane 5) and the $\Delta$:215–426 human p55-TNF-R (lane 6). The lane marked Mr is the one of the molecular weight markers.

FIG. 1B: shows the same receptor size analysis, however without acidification prior to immunoprecipitation.

FIG. 2 schematically illustrates the structure of the wild type human p55-TNF-R and of three truncated forms thereof, i.e. truncated at amino acid 310 (the $\Delta$:310–426 human p55-TNF-R mutant), at amino acid 244 (the $\Delta$:244–426 human p55-TNF-R mutant), and at amino acid 215 (the $\Delta$:215–426 human p55-TNF-R mutant).

FIG. 3B illustrates the cytocidal effects of monoclonal antibodies against the human p55-TNF-R in the same cells as FIG. 3A.

Figure 1A:
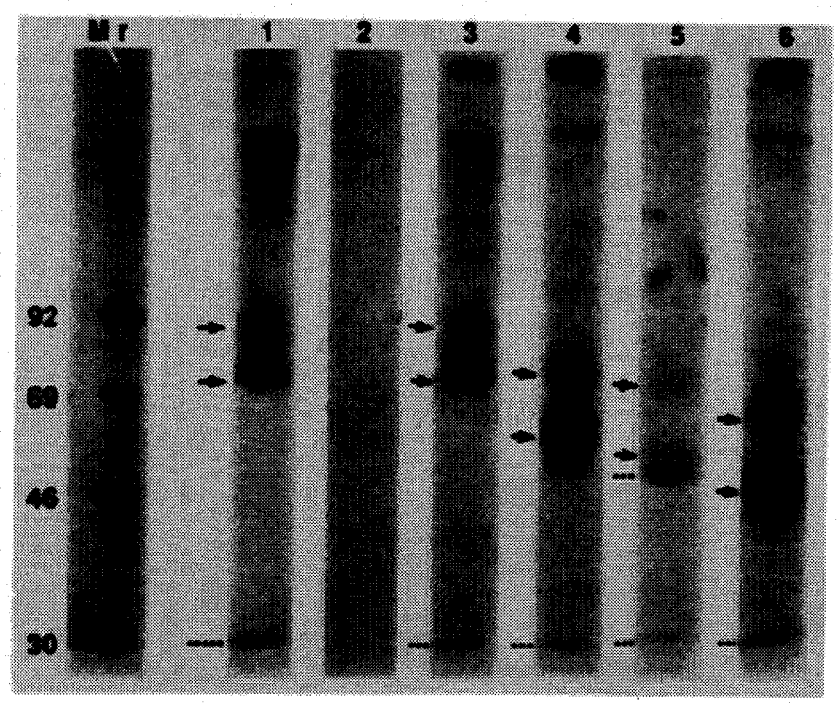
FIGS. 1A and 1B: show the different receptor sizes after covalent cross-linking with labelled TNF, immunoprecipitation and SDS-PAGE analysis. The patterns shown are as follows.

The following examples illustrate the invention without limiting it thereto.

EXAMPLE 1

Detection of Aggregates of Human TNF-Rs in the Analysis of their Sizes

A9 cells, as well as cells expressing the wild type and mutant forms of the human p55-TNF-R, and HeLa cells were detached by incubation in PBS containing 5 mM EDTA and, after rinsing with binding buffer, were suspended in aliquots of $5\times10^7$ cells in 1 ml binding medium, containing radiolabelled TNF. After incubation with occasional shaking for 4 hrs. on ice, the cells were washed once with Dulbecco's balanced salt solution (PBS+) and incubated for 20 min. in the same buffer containing 1 mM bis(sulfosuccinimidyl)suberate (Pierce). Cross-linking was stopped by adding Tris-HCl and glycine-HCl, pH 7.4 (both to a final concentration of 100 nM) followed by two washes with PBS+. The cells were then extracted for 1 hr. at 4° C., using 600 µl of a lysis buffer containing 20 mM Hepes, pH 7.4, 150 mM NaCl, 1% deionised Triton X-100 1 µg/ml leupeptin and 1 mM-phenylmethylsulfonyl fluoride. After centrifugation for 30 min at 10.000×g the cell extracts were divided into two equal portions. One (portion A) was acidified by adding 90 µl 1M glycine-HCl buffer pH 2.5 and, after 1 hr. incubation on ice, neutralized with 30 µl 1M NaOH. To this portion of the extracts as well as to the other one (B), monoclonal antibodies against the human p55-TNF-R were added. After 12 hrs further incubation at 4° C., 20 µl protein-A Sepharose beads (Pharmacia), equilibrated with PBS+. were added and, following 60 min incubation at 4° C., washed three times with the lysis buffer containing 2M KCl, and two times with PBS. The beads were resuspended in 15 µl sample buffer containing 4% (w/v) SDS and 6% (v/v) β-mercaptoethanol and boiled for 3 min. The superantant was analysed by SDS-PAGE (10% polyacrylamide) followed by autoradiography.

Figure 1B:
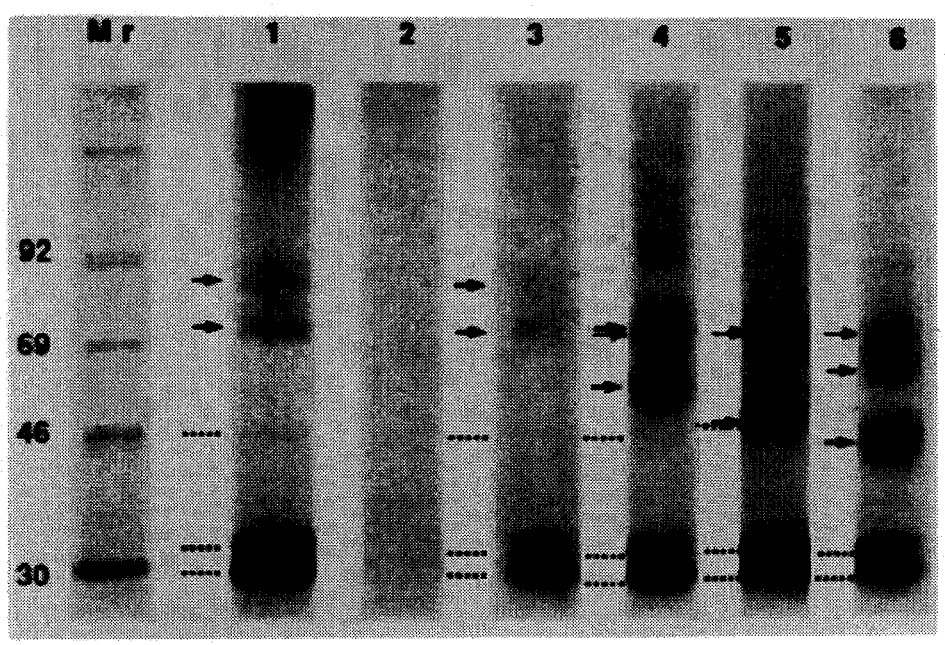

As shown in FIGS. 1A and 1B, the receptors for TNF exist in aggregated forms in cells exposed to TNF. These figures present the SDS-PAGE analysis of the full-length and truncated forms of the human p55-TNF-Rs (see the schematic representation of the different forms in FIG. 2) expressed in murine A9 cells and tagged by applying the radio-labelled TNF on the cells followed by cross-linking.

The receptors were immunoprecipitated from detergent extracts of the cells following acidification of the extracts, in order to dissociate non-covalent aggregates of proteins (A) or without such acidification (B). The patterns of the labelled proteins, precipitated from extracts of HeLa cells (lane 1), from extracts of non-transfected A9 cells (lane 2), from extracts of A9 cells expressing the wild type human p55-TNF-R (3), and from extracts of A9 cells expressing the Δ:310–426 human p55-TNF-R (4), the Δ:244–426 human p55-TNF-R (5) and the Δ:215:426 human p55-TNF-R (6) mutants are shown in comparison to the migration of molecular weight markers (Mr). Labelled bands whose sizes correspond to the expressed human receptors, tagged by cross-linking to either one or to two labelled TNF molecules, are denoted with solid arrows (sizes of 72 and 89 kD for the full length receptor, 59 and 76 kD for t he Δ:310–426 human p55-TNF-R, 51 and 68 kD for the Δ:244–426 human p55-TNF-R and 48 and 65 kD for the Δ:215:426 human p55-TNF-R). The labelled bands whose sizes correspond to the full-length murine receptors, cross-linked either to one or to two TNF molecules (72 and 89 kD) are denoted with empty arrows, and the bands which correspond to cross-linked monomers, dimers and trimers of TNF (17, 34 and 51 kilodaltons)—by stippled lines.

The antibodies applied for immunoprecipitation in this analysis of the receptor size, recognized specifically the receptors of human origin (solid arrows). These antibodies did not precipitate TNF receptors from extracts of non-transfected A9 cells (compare lanes 1 and 2). However, in application of these antibodies to extracts of the A9 cells which express the human p55-TNF-R, it was found that, together with the human receptors, the antibodies precipitated also some of the murine receptors, which were easily distinguishable from the truncated human receptors by their full length size (empty arrows) (lanes 3–6 in FIG. 1B), implying that the TNF receptors exist in the cells as aggregates, containing both receptors of human and of murine origin. Consistently with this notion, it was found that if, prior to immunoprecipitation, the cell extracts were exposed to low pH, in order to disrupt non-covalent association between the receptors, the human receptors could still be precipitated. However, the precipitation of the murine receptors was abolished (compare FIG. 1A to FIG. 1B).

EXAMPLE 2

A. Construction of Mutant p55-TNF-Rs

The cDNA of the human TNF-RI (see EP application 90 12 4133.1) was cut with BanII (at nucleotides 218–222) and NheI (at nucleotides 1723 and 1728), resulting in removal of large parts of the non-coding regions including an ATG in the 5' non-coding region and a multiple GTn(n=4–8) in the 4' non-coding region. Site directed mutagenesis of this shortened form of the cDNA was carried out using the "Altered Sites" (mutagenesis) kit of Promega. Stop codons were introduced in the following points: After leucine 309 (mutant Δ:310–426) using the oligonucleotide: 5=-CCC CAA CCT CTA GAA GTG GGA GG-3' and after leucine 214 (mutant Δ:215–426) using the oligonucleotide: 5'-AGT CCA AGC TCT AGA CCA TTG TTT GTG G-3' (FIG. 1). The wild type and mutated cDNAs were introduced to an eukaryotic expression vector. For the generation of the Δ:244–426 mutant, the expression vector containing the wild type cDNA was cut with HindIII. The 3.9 Kb fragment was isolated and then, after fill-in of the protruding ends, religated, thus replacing amino acid 244 by a stop codon.

B. Expression of the Wild Type and the Mutant Receptors in Cultured Cells

Cells of murine A9, L929, NiH3T3 and the hamster BHK lines were cultured with Dulbecco's Minimal Essential Medium (DMEM), containing 10% fetal calf serum, 100 units/ml penicillin and 100 µg/ml streptomucin. The expression constructs encoding the wild type and the mutant receptors were cotransfected together with the neomycin resistance conferring plasmid pSV2neo into these cells, using the calcium phosphate precipitation method. After 10 to 14 days selection in growth medium containing 500 µg/ml G418, resistant colonies were isolated and checked for expression of the human p55 TNF-R by measuring TNF binding to the cells.

FIG. 2 illustrates the structure of the wild type human p55-TNF-receptor. It consists of icons depicting the full length human p55-TNF-R and the truncated forms of this receptor created by site-directed mutagenesis. Using these oligonucleotides, stop codons were introduced into the intracellular domain of the receptor at amino acids 310 (the Δ:310–426 human p55-TNF-R mutant), 244 (the Δ:244–426 human p55-TNF-R mutant), and 215 (the Δ:215:426 human p55-TNF-R mutant).

Figure 3A:
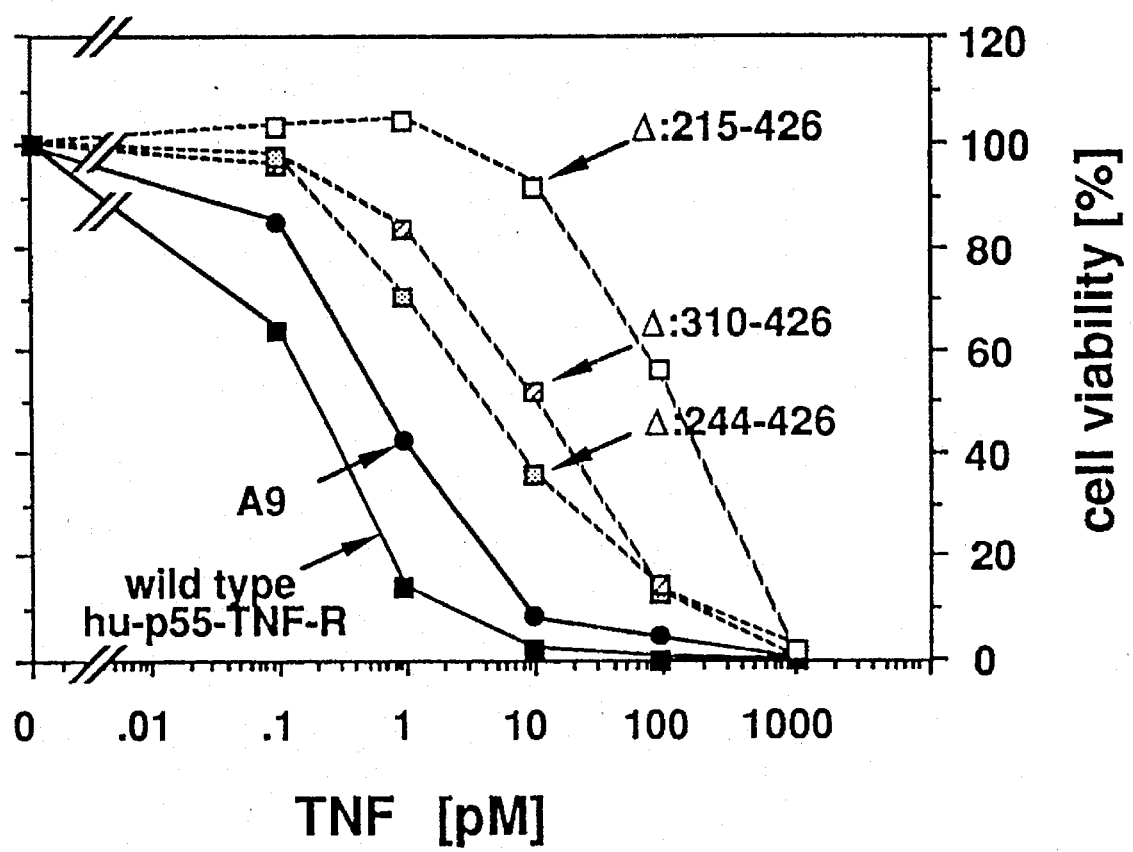
FIG. 3A illustrates the cytocidal effects of TNF in A9 cells expressing the full length human p55-TNF-R, and in A9 cells expressing the cytoplasmic deletion mutants thereof ($\Delta$:310–426, $\Delta$:244–426 and $\Delta$:215:426 human p55-TNF-R).
Figure 4A:
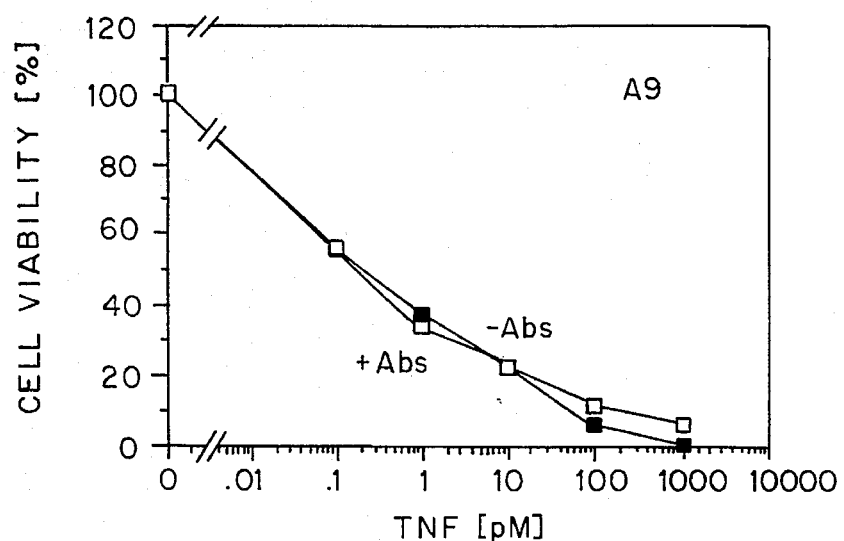
FIGS. 4A, 4B and 4C show that treatment of A9 cells which express a cytoplasmic deletion mutant of the human p55-TNF-R antibodies to the receptor restores their sensitivity to the cytocidal effect of TNF.
Figure 4B:
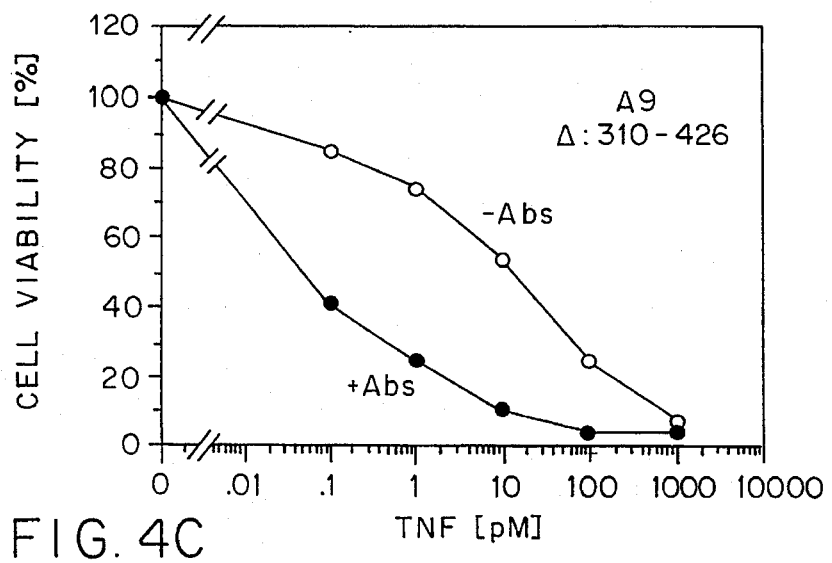
Figure 4C:
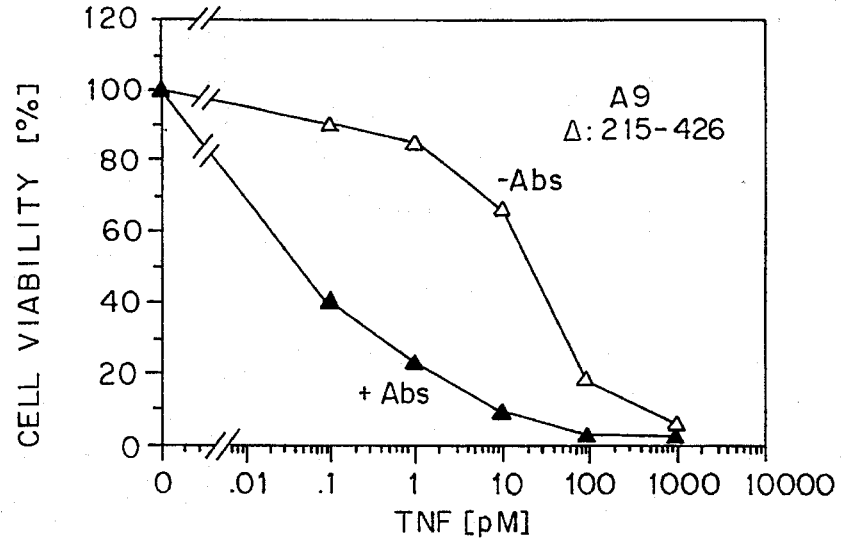

FIGS. 3 and 4 provide further evidence for the existence of the cell-surface TNF-R as aggregates as well as for two other points, namely that aggregation of functional receptors is necessary for the activity of these receptors, as well as that involvement of non-functional receptors in this aggregation results in effective inhibition of TNF function.

FIG. 3 illustrates the cytocidal effects of TNF (A) and of monoclonal antibodies against the human p55-TNF-R (B) in A9 cells, in A9 cells expressing the full length human p55-TNF-R, and in A9 cells expressing the cytoplasmic deletion mutants of the human p55-TNF-R (the Δ:310–426 human p55-TNF-R, the Δ:244–426 human p55-TNF-R, and the Δ:215:426 human p55-TNF-R.

Cells were seeded into 96-well plates, 24 hrs. before the assay, at a density of 30,000 cells/well. The TNF and the monoclonal antibodies, were applied simultaneously with CHI (50 µg/ml). After further 11 hrs. incubation at 37° C., viability of the cells was assessed in a neutral red uptake assay. The two monoclonal antibodies were applied at equal amounts which summed up to the concentration specified in the figure.

Turning now to FIG. 4, the cytocidal effect of TNF, applied together with cycloheximide (CHI) (50 µg/ml to A9 cells (A), A9 cells expressing the Δ:310–426 human p55-TNF-R (B) and A9 cells expressing the Δ:215:426 hum,an p55-TNF-R (C), was examined in the presence and absence of antibodies to the human p55-TNF-R. Similar sensitization by the antibodies to the cytocidal effect of TNF was observed in A9 cells expressing the Δ:244–426 human p66-TNF-R mutant.

Thus, while having a pronounced cytocidal effect in the A9 cells which express the full-length human p55-TNF-R, the antibodies had no effect at all in cells expressing any of the three truncated forms of the receptor, suggesting that these truncated forms are not functional. Furthermore, testing the effect of TNF itself on the cells revealed that, in contrast to the full-length human p55-TNF-R receptors, whose expression results in increased sensitivity of the A9 cells to TNF, the truncated forms of the receptors conveyed a decreased responsiveness to the cytocidal effect of TNF.

This decrease could be observed in clones of A9 cells, expressing either one of the truncated forms of the receptors, at extents which seemed roughly proportional to the extent of receptor expression. Sensitivity to TNF could be recovered by applying on these cells antibodies to the h-p55-TNF-R, confirming that the decrease in response to TNF reflects an inhibitory effect of the truncated human receptors on the function of the full length rodent receptors.

EXAMPLE 3

Creation of Multimers of the Soluble Forms of TNF-Rs by Chemical Cross-Linking of these Proteins a) Introduction of cysteine or, alternatively, of Biotin, to the C-termini of the soluble receptors:

Procedure I: Samples of the soluble forms of either the human p55- or the human p75-TNF-R are incubated with cysteine amide, or alternatively, with Biotin amide

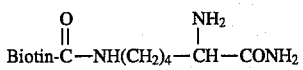

and with carboxypeptidase Y. In the presence of excess of the cysteine amide or the Biotin amide the enzymatic reaction leads primarily to incorporation to these compounds to the C-termini of the soluble receptors.

Procedure II: The reactions are carried out as above, except that the amino acid within the receptor chosen to be the C-terminal for the soluble receptors is lysine and that lysine endopeptidase is applied instead of carboxypeptidase. Use of this enzyme assures that, beside removal of a single amino acid from the C-terminus of the soluble receptor, no further truncation of the soluble receptor takes place.

b) Use of soluble receptors, to whose C-termini cysteine was introduced, for formation of dimers of the soluble receptors: Receptors to whose C-termini cysteins were introduced as described above, are cross-linked to form dimers, using activated linkers of either one of the following two formulae:

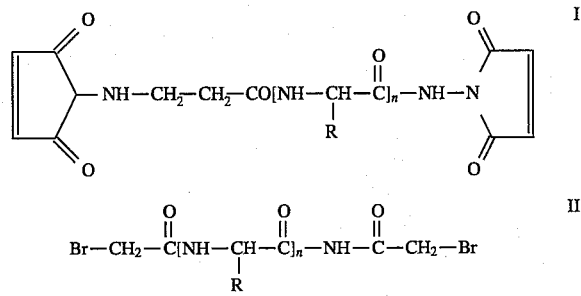

Linkers of different lengths can be employed. The function of the products will be compared to each other and thus the optimal linker length will be defined. In case free cysteines turn out to be present within the soluble receptors, they will be blocked before the introduction of cysteine to the C-termini, by way of alkylation.

c) Use of soluble receptors, to whose C-termini Biotin was introduced, for formation of tetramers of the soluble receptors, as well as more complex structures of the receptors: The soluble receptors to whose C-termini Biotin was introduced, as described above, are cross-linked with Avidin. Each Avidin contains four Biotin binding sites. In that way tetramers of the receptors are formed. Alternatively, part of the four binding sites in the Avidin serve for binding other proteins to which Biotin was linked. In that way, several Avidin molecules are linked to each other, resulting in formation of higher aggregates of the soluble forms of the human TNF-Rs. This approach allows also the binding of additional molecules to the soluble forms of the TNF-Rs (e.g. Fc portions of antibodies).

Alternatively, Avidin may be replaced with Streptavidin, the procedure itself remaining the same.

d) Formation of multimers of the soluble receptors by cross-linking cysteines located within the receptor's sequence:

Such multimers of TNF receptors are formed by linking the molecules of soluble forms of the TNF-Rs to each other using cross-linking reagents specific to amine groups or to thiols. (The later following partial reduction of the cysteines in the soluble receptors with β-mercapthoethanol or dithiothreitol).

e) Formation of liposomes containing multiple molecules of the truncated receptors:

Procedure I: Liposomes expressing any Biotin-containing protein on their surface can be applied for that purpose. Soluble forms of the TNF-Rs to whose C-termini Biotin was linked, are linked to these liposomes with the use of (the tetravalent) Avidin.

Procedure II: Recombinant TNF receptors, truncated in the intracellular domains, but containing the transmembrane domains, are produced as described in Example 2. They are then incorporated into liposomes by dissociation in detergents, followed by their reconstitution in the presence of lipids by removal of the detergents.

f) Isolation of soluble receptor multimers with highest inhibitory effect on TNF function:

Preparations of soluble receptor dimers or multimers are fractionated chromatographically, and fractions showing highest inhibitory effects on TNF function are further analyzed, to define the structures optimal for TNF inhibition. Alternatively, affinity purification of the optimal inhibitors is performed, by applying preparations of soluble receptor dimers or multimers to TNF-affinity columns.

EXAMPLE 4

Creation of Recombinant DNA Molecules Comprising Nucleotide Sequences Coding for the Multimers of the Soluble TNF-Rs and their Expression The dimers and higher multimers of the soluble receptors can also be prepared by genetic engineering techniques and their preparation encompasses all the tools used in these techniques. Thus DNA molecules are provided which comprise the nucleotide sequence coding for such dimers or oligomers. These DNA molecules can be genomic DNA, cDNA, synthetic DNA and a combination thereof.

Creation of DNA molecules coding for a dimer of soluble receptors is carried out by ligating the cDNA sequence encoding the soluble form of a TNF-R to a sequence encoding a linker peptide and then further to a synthetic polynucleotide encoding the translation of the soluble receptor in the reverse orientation—from the original C-terminus to the N-terminus and lacking the sequence of the leader peptide.

Polymeric forms of the soluble receptors can be created, as mentioned above, by forming recombinant truncated receptors, deficient of intracellular domains but containing transmembrane domains, and incorporating them, by membrane reconstitution techniques, into liposomes.

Expression of the recombinant proteins can be effected in eukaryotic cells, bacteria or yeasts, using the appropriate expression vectors. Any method known in the art may be employed.

For example, the DNA molecules coding for the multimers of the soluble forms of the TNF-Rs obtained by the above methods are inserted into appropriately constructed expression vectors by techniques well known in the art (see Maniatis et al., op cit.). Double-stranded cDNA is linked to plasmid vectors by homopolymeric tailing or by restriction linking involving the use of synthetic DNA linkers or blunt-ended ligation techniques. DNA ligases are used to ligate the DNA molecules and undesirable joining is avoided by treatment with alkaline phosphatase.

In order to be capable of expressing a desired protein, an expression vector should comprise also specific nucleotide sequences containing transcriptional and translational regulatory information linked to the DNA coding for the desired protein in such a way as to permit gene expression and production of the protein. First, in order for the gene to be transcribed, it must be preceded by a promoter recognizable by RNA polymerase, to which the polymerase binds and thus initiates the transcription process. There are a variety of such promoters in use, which work with different efficiencies (strong and weak promoters). They are different for prokaryotic and eukaryotic cells.

The promoters that can be used in the present invention may be either constitutive, for example, the int promoter of bacteriophage λ, the bla promoter of the β-lactamase gene of pBR322, and the CAT promoter of the chloramphenicol acetyl transferase gene of pPR325, etc., or inducible, such as the prokaryotic promoters including the major right and left promoters of bacteriophage λ ($P_L$ and $P_R$), the trp, recA, lacZ, LacI, ompF and gal promoters of E. Coli, or the tro-lac hybrid promoter, etc. (Glick, B. R. (1987) J. Ind. Microbiol. 1:227–282).

Besides the use of strong promoters to generate large quantities of mRNA, in order to achieve high levels of gene expression in prokaryotic cells, it is necessary to use also ribosome-binding sites to ensure that the mRNA is efficiently translated. One example is the Shine-Dalgarno sequence (SD sequence) appropriately positioned from the initiation codon and complementary to the 3'-terminal sequence of 16S RNA.

For eukaryotic hosts, different transcriptional and translational regulatory sequences may be employed, depending on the nature of the host. They may be derived from viral sources, such as adenovirus, bovine papilloma virus, Simian virus, or the like, where their regulatory signals are associated with a particular gene which has a high level of expression. Examples are the TK promoter of Herpes virus, the SV40 early promoter, the yeast gal4 gene promoter, etc. Transcriptional initiation regulatory signals may be selected which allow for repression and activation, so that expression of the genes can be modulated.

The DNA molecule comprising the nucleotide sequence coding for the TNF multimers of the invention and the operably linked transcriptional and translational regulatory signals is inserted into a vector which is capable of integrating the desired gene sequences into the hose cell chromosome. The cells which have stably integrated the introduced DNA into their chromosomes can be selected by also introducing one or more markers which allow for selection of host cells which contain the expression vector. The marker may provide for prototrophy to an auxotropic host, biocide resistance, e.g., antibiotics, or heavy metals, such as copper, or the like. The selectable marker gene can either be directly linked to the DNA gene sequences to be expressed, or introduced into the same cell by co-transfection. Additional elements may also be needed for optimal synthesis of single chain binding protein mRNA. These elements may include splice signals, as well as transcription promoters, enhancers, and termination signals. cDNA expression vectors incorporating such elements include those described by Okayama, H., (1983) Mol. Cel. Biol. 3:280.

In a preferred embodiment, the introduced DNA molecule will be incorporated into a plasmid or viral vector capable of autonomous replication in the recipient host. Factors of importance in selecting a particular plasmid or viral vector include: the ease with which recipient cells that contain the vector may be recognized and selected from those recipient cells which do not contain the vector; the number of copies of the vector which are desired in a particular host; and whether it is desirable to be able to "shuttle" the vector between host cells of different species.

Preferred prokaryotic vectors include plasmids such as those capable of replication in E. coli, for example, pBR322, ColEl, pSC101, pACYC 184, etc. (see Maniatis et al., *Molecular Cloning: A Laboratory Manual*, op.cit.); Bacillus plasmids such as pC194, pC221, pT127, etc. (Gryczan, T., *The Moleculr Biology of the Bascilli*, Academic Press, N.Y. (1982), pp. 307–329); Streptomyces plasmids including pIJ101 (Kendall, K. J. et al., (1987) J. Bacteriol. 169:4177–4183); Streptomyces bacteriophages such as ØC31 (Chater, K. F. et al., in: *Sixth International Symposium on Actinomycetales Biology*, Akademiai Kaido, Budapest, Hungary (1986), pp. 45–54), and Pseudomonas plasmids (John, J. F., et al. (1986) Rev. Infect. Dis. 8:693–704), and Izaki, K. (1978) Jpn. J. Bacteriol. 33:729–742).

Preferred eukaryotic plasmids include BPV, vaccinia, SV40, 2-micron circle, etc., or their derivatives. Such plasmids are well known in the art (Botstein, D., et al. (1982) Miami Wint. Symp. 19:265≧274; Broach, J. R., in: *The Molecular Biology of the Yeast Saccharomyces: Life Cycle and Inheritance*, Cold Spring Harbor Laboratory, Cold Spring Harbor, N.Y., pp. 445–470 (1981); Broach, J. R., (1982) Cell 28:203–204; Bollon, D. P. et al. (1980) J. Clin. Hematol. Oncol. 10:39–48; Maniatis, T., in: *Cell Biology: A Comprehensive Treatise, Vol 3: Gene Expression:* Academic Press, N.Y., pp. 563–608 (1980)).

Once the vector or DNA sequence containing the construct(s) has been prepared for expression, the DNA construct(s) may be introduced into an appropriate host cell by any of a variety of suitable means: transformation, transfection, conjugation, protoplast fusion, electroporation, calcium phosphate-precipitation, direct microinjection, etc.

Host cells to be used in this invention may be either prokaryotic or eukaryotic. Preferred prokaryotic hosts include bacteria such as E. coli, Bacillus, Streptomyces, Pseudomonas, Salmonella, Serratia, etc. The most preferred prokaryotic host is E. coli. Bacterial hosts of particular interest include E. coli K12 strain 294 (ATCC 31446), E. coli K1776 (ATCC 31537), E. coli W3110 (F⁻, lambda⁻, prototropic (ATCC 27325), and other enterobacterium such as Salmonella typhimurium or Serratia marcescens and various Pseudomonas species. Under such conditions, the protein will not be glycosylated. The prokaryotic host must be compatible with the replicon and control sequences in the expression plasmid.

Preferred eukaryotic hosts are mammalian cells, e.g., human, monkey, mouse and chinese hamster ovary (CHO) cells, because they provide post-translational modifications to protein molecules including correct folding or glycosylation at correct sites. Also yeast cells can carry out post-translational peptide modifications including glycosylation. A number of recombinant DNA strategies exist which utilize strong promoter sequences and high copy number of plasmids which can be utilized for production of the desired proteins in yeast. Yeast recognizes leader sequences on cloned mammalian gene products and secretes peptides bearing leader sequences (i.e., pre-peptides).

After the introduction of the vector, the host cells are grown in a selective medium, which selects for the growth of vector-containing cells. Expression of the cloned gene sequence(s) results in the production of the desired multimers of the soluble forms of the TNF-Rs.

Purification of the recombinant proteins is carried out using monoclonal antibodies to the soluble forms of the TNF-Rs, or by affinity purification on ligand (TNF) columns.

All references cited herein, including journal articles, or abstracts, published or corresponding U.S. or foreign patent applications, issued U.S. or foreign patents, or any other references, are entirely incorporated by reference herein, including all data, tables, figures, and text presented in the cited references. Additionally, the contents of the references cited within the references cited herein are also entirely incorporated by reference.

Reference to known method steps, conventional method steps, known methods or conventional methods is not in any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the generic concept of the present invention. Therefore, such adaptions and modifications are intended to be comprehended within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein.

We claim:

1. A multimer having the ability to interfere with the binding of tumor necrosis factor to its receptors and to block the effects of tumor necrosis factor, wherein said multimer comprises two or more monomers, each said monomer consisting of a soluble form of a tumor necrosis factor receptor or a salt thereof.

2. A multimer in accordance with claim 1 in dimeric form.

3. A multimer in accordance with claim 1 in trimeric form.

4. A multimer in accordance with claim 1 wherein each said monomer has an amino acid sequence corresponding to that of tumor necrosis factor binding protein-I.

5. A multimer in accordance with claim 1 wherein each said monomer has an amino acid sequence corresponding to that of tumor necrosis factor binding protein-II.

6. A multimer in accordance with claim 1, wherein said monomers include at least one monomer having an amino acid sequence essentially corresponding to that of tumor necrosis factor binding protein-I and at least one monomer having an amino acid.

7. A multimer in accordance with claim 1 said multimer being encapsulated in a liposome.

* * * * *

UNITED STATES PATENT AND TRADEMARK OFFICE
CERTIFICATE OF CORRECTION

PATENT NO. : 5,478,925
DATED : December 26, 1995
INVENTOR(S) : D. WALLACH et al.

It is certified that error appears in the above-indentified patent and that said Letters Patent is hereby corrected as shown below:

Claim 6, column 14, line 28, delete "essentially";
line 30, after "amino acid" insert
--sequence corresponding to that of tumor necrosis factor binding protein-II--.

Signed and Sealed this

Twenty-fifth Day of March, 1997

Attest:

BRUCE LEHMAN

Attesting Officer

Commissioner of Patents and Trademarks

Adverse Decision In Interference

Patent No. 5,478,925, David Wallach, Cord Brakebusch, MULTIMERS OF THE SOLUBLE FORMS OF TNF RECEPTORS, THEIR PREPARATION AND PHARMACEUTICAL COMPOSITIONS CONTAINING THEM, Interference No. 103,854, final judgment adverse to the patentees rendered August 11, 2000, as to claims 1-7.

*(Official Gazette May 15, 2001)*